United States Patent
Tarara et al.

[11] Patent Number: 5,094,682
[45] Date of Patent: Mar. 10, 1992

[54] 1-METHOXYPYRIMIDINYL-N-NITROPHE-NYL-1H-1,2,4-TRIAZOLE-3-SULPHONA-MIDES AND THEIR USE AS HERBICIDES

[75] Inventors: Gerhard Tarara; Gabriele Krüger; Peter Wegner; Richard Rees; Gerhard Johann, all of Berlin, Fed. Rep. of Germany

[73] Assignee: Schering Aktiengesellschaft, Fed. Rep. of Germany

[21] Appl. No.: 582,251

[22] Filed: Sep. 14, 1990

[30] Foreign Application Priority Data

Sep. 14, 1989 [DE] Fed. Rep. of Germany ....... 3931060

[51] Int. Cl.$^5$ .................. A01N 43/54; A01N 43/653; C07D 403/04
[52] U.S. Cl. ......................................... 71/92; 544/321
[58] Field of Search ............................. 544/321; 71/92

[56] References Cited

U.S. PATENT DOCUMENTS 4,889,553 12/1989 Rowson et al. .................... 71/92
4,959,094 9/1990 Wegner et al. .................... 71/92

Primary Examiner—Patricia L. Morris
Attorney, Agent, or Firm—Ostrolenk, Faber, Gerb & Soffen

[57] ABSTRACT

The invention relates to new 1-(methoxypyrimidinyl)-N-nitrophenyl-1H-1,2,4-triazole-3-sulphonamides of general formula I

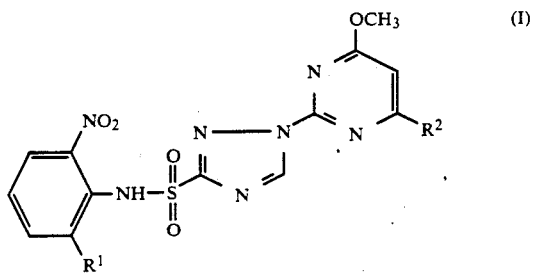

in which $R^1$ and $R^2$ have the meanings given in the description, processes for their preparation and their use as herbicides.

12 Claims, No Drawings

1-METHOXYPYRIMIDINYL-N-NITROPHENYL-1H-1,2,4-TRIAZOLE-3-SULPHONAMIDES AND THEIR USE AS HERBICIDES

The invention relates to new 1-(methoxypyrimidinyl)-N-nitrophenyl-1H-1,2,4-triazole-3-sulphonamides, processes for their preparation and their use as herbicides.

In EP 246 749 there are claimed herbicidal triazole-sulphonamides of the formula:

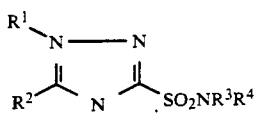

and salts thereof, where:

$R^1$ represents hydrogen or a substituted or unsubstituted alkyl, alkenyl, alkynyl, cycloalkyl, aryl, aralkyl, acyl, alkoxycarbonyl, aminocarbonyl, sulphonyl or heterocyclic group;

$R^2$ represents hydrogen, halo, cyano, hydroxy, mercapto, a substituted or unsubstituted alkyl, alkenyl, alkynyl, alkoxy, alkylthio, alkylsulphinyl, alkylsulphonyl, acyl, alkoxycarbonyl, aminocarbonyl, aryl or amino group, or a heterocyclic group;

$R^3$ represents a substituted heterocyclic, benzheterocyclic, aryl or aralkyl group; and $R^4$ represents hydrogen, a substituted or unsubstituted alkyl, alkenyl, alkynyl, acyl, alkylsulphonyl, alkoxycarbonyl, aminocarbonyl, aralkyl, or a group of the formula:

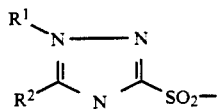

where $R^1$ and $R^2$ are as defined hereinbefore.

We have now found that a particular group of compounds within this broad claim have especially valuable properties. The selection of this group could not be predicted from the prior document nor could it be predicted that this group of compounds would show the particular advantages.

According to the invention there are provided 1-(methoxypyrimidinyl)-N-nitrophenyl-1H-1,2,4-triazole-3-sulphonamides of general formula I

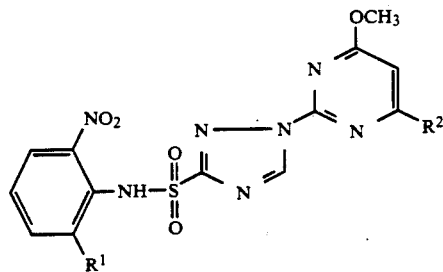

in which
$R^1$ is methyl, methoxy, allyloxy or propargyloxy, and
$R^2$ is methyl or methoxy, with the proviso that $R^1$ is not methyl, if $R^2$ is methoxy.

The compounds of the invention are thus 1H-1,2,4-triazole-3-sulphonamide derivatives, carrying a phenyl group (with defined substituents) on the sulphonamide linkage and in which the triazole is substituted in the 1-position by a 4,6-dimethoxypyrimidin-2-yl group or a 4-methoxy-6-methylpyrimidin-2-yl group.

The compounds of the invention are characterised by good herbicidal activity and especially high activity against important rice weeds, combined with good crop selectivity, in paddy rice. This combination of good activity against important rice weeds with good crop selectivly in paddy rice is not seen in the compounds disclosed in EP 246 749.

The compounds of the invention of general formula I can be prepared for example

A) be reacting a compound of general formula II

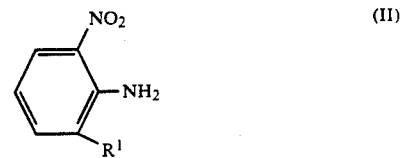

where $R^1$ has the meaning given above, with a sulphonyl chloride of general formula III

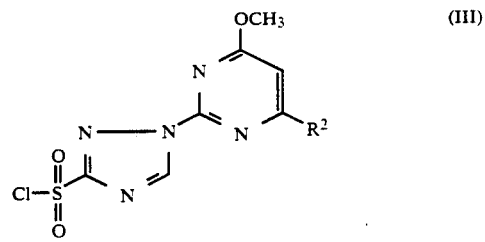

where $R^2$ has the meaning given above, in a suitable solvent in the presence of an acid acceptor, or B) by reacting a compound of general formula IV

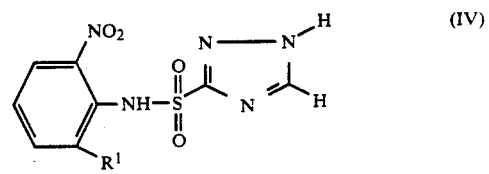

where $R^1$ has the meaning given above, with a compound of general formula V

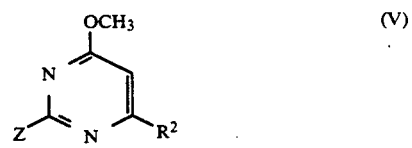

where Z is leaving group, such as halogen or an alkyl- or arylsulphonyl group and $R^2$ has the meaning given above, in a suitable solvent in the presence of an acid binding agent.

The individual reaction variants are preferably carried out in the presence of a diluent. For this purpose there can be used solvents which are inert to the reactants.

Examples of such solvents or diluents are water, aliphatic, alicyclic and aromatic hydrocarbons, that can optionally be chlorinated, such as for example hexane, cyclohexane, petroleum ether, naphtha, benzene, toluene, methylene chloride, chloroform, carbon tetrachloride, ethylene dichloride and trichloroethane, ethers, such as for example diisopropyl ether, dibutyl ether, propylene oxide, dioxane and tetrahydrofuran, ketones such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphoxides, such as for example dimethyl sulphoxide and sulpholane, and bases, such as for example pyridine.

The reaction is suitably carried out between room temperature and the boiling point of the particular reaction mixture. The reaction can be carried out under atmospheric pressure but if desired higher or lower pressures can be used.

The process variant A) is preferably carried out in the presence of a chlorinated hydrocarbon, such as methylene chloride or dichloroethane, in the presence of a catalyst and/or acid acceptor. Examples of these are tertiary amines, such as triethylamine, diisopropylethylamine, N-methylmorpholine, 4-dimethylaminopyridine and pyridine. Pyridine can act as both catalyst and solvent in this reaction.

The process variant B) is preferably carried out in an inert solvent, such as dioxane, tetrahydrofuran, dimethylformamide or N-methylpyrrolidinone optionally in the presence of a catalyst. Examples of acid binding agents are metal hydrides, tertiary amines, such as triethylamine and diisopropylethylamine, and inorganic bases such as for example alkali metal and alkaline earth metal hydroxides and carbonates.

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by recrystallisation.

The compounds of the invention are, as a rule, colourless or odourless crystals that are slightly soluble in water and in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of formula II, III, IV and V can be prepared as described in the literature and especially as described in EP 246 749.

As stated previously the compounds of the invention show good herbicidal activity. This activity is seen against monocotyledonous and dicotyledonous weeds with good selectivity in various crops, such as for example paddy rice.

The compounds of the invention thus generally have activity also against the following plant species: Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monochoria, Fimbristylis, Eleocharis, Ischaemum and Apera.

The rates of use vary between 0.01 and 1 kg/ha, depending on the species in pre and post emergent application.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 38, Nov. 3, 1988, under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitable be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

(A) Wettable Powder

(1)

25 percent by weight active ingredient
60 percent by weight kaolin
10 percent by weight silicic acid
5 percent by weight of a mixture of calcium lignosulphonate and the sodium salt of N-methyl-N-oleyltaurine

(2)

40 percent by weight active ingredient
25 percent by weight bentonite
25 percent by weight silicic acid
10 percent by weight of a mixture of calcium lignosulphonate and alkylphenyl polyglycol ether

(B) Paste 45 percent by weight active ingredient
5 percent by weight sodium aluminium silicate
15 percent by weight cetyl polyglycol ether with 8 mol of ethylene oxide
2 percent by weight spindle oil
10 percent by weight polyethylene glycol
23 percent by weight water

(C) Emulsifiable Concentrate 25 percent by weight active ingredient
15 percent by weight cyclohexanone
55 percent by weight xylene
5 percent by weight of a mixture of calcium dodecylbenzenesulphonate and nonylphenolpolyoxyethylene.

The following examples illustrate the preparation of compound according to the invention.

EXAMPLE 1

1-(4,6-Dimethoxypyrimidin-2-yl)-N-(6-nitro-2-propargyloxyphenyl)-1H-1,2,4-triazole-3-sulphonamide A mixture of 3.23 g (10 mmol) N-(6-nitro-2-propargyloxyphenyl)-1H-1,2,4-triazole-3-sulphonamide and 2.76 g (20 mmol) potassium carbonate in 25 ml dimethylformamide was heated under a protective gas for 10 minutes at 50° C. After cooling to 0° C. and addition of 2.18 g (10 mmol) 4,6-dimethoxy-2-methylsulphonylpyrimidine, the mixture was warmed and stirred for 20 hours. It was then stirred into to 300 ml ice-cold saturated aqueous sodium chloride and acidified with hydrochloric acid (pH 4). The crystals were removed by suction filtration and purified by silica gel chromatography using a mixture of hexane and ethyl acetate (0 to 100% ethyl acetate).
Yield: 2.77 g = 60% of theory
M.p.: 177°–181° C.

In a similar manner to these processes the following compounds were prepared.

| Example | Compound | Physical constant |
|---|---|---|
| 2 | 1-(4-methoxy-6-methylpyrimidin-2-yl)-N-(2-methyl-6-nitrophenyl)-1H-1,2,4-triazole-3-sulphonamide | mp 203–204° C. |
| 3 | 1-(4,6-dimethoxypyrimidin-2-yl)-N-(2-methoxy-6-nitrophenyl)-1H-1,2,4-triazole-3-sulphonamide | mp 226–229° C. |
| 4 | 1-(4,6-dimethoxypyrimidin-2-yl)-N-(2-allyloxy-6-nitrophenyl)-1H-1,2,4-triazole-3-sulphonamide | mp 134–137° C. |
| 5 | 1-(4-methoxy-6-methylpyrimidin-2-yl)-N-(2-methoxy-6-nitrophenyl)-1H-1,2,4-triazole-3-sulphonamide | mp 193–196° C. |
| 6 | 1-(4-methoxy-6-methylpyrimidin-2-yl)-N-(2-allyloxy-6-nitrophenyl)-1H-1,2,4-triazole-3-sulphonamide | mp 179–184° C. |
| 7 | 1-(4-methoxy-6-methylpyrimidin-2-yl)-N-(6-nitro-2-propargyloxyphenyl)-1H-1,2,4-triazole-3-sulphonamide | mp 187–191° C. |

The following examples illustrate the possibilities for areas of use of the compounds of the invention.

EXAMPLE A

In a greenhouse, the compounds noted in the table were applied at the rates mentioned. For this the formulated active ingredients were pipetted onto the water surface of vessels containing 1500 ml water. Test plants that were treated were in the 1 to 5 leaf stages. Three weeks after the application, the damage to the plants was assessed according to the following scheme. The compounds of the invention showed good activity against *Cyperus difformis* and *Eleocharis acicularis*, coupled with selectivity in paddy-rice.

In the following table:
0 = no damage
1 = slight damage
2 = medium damage
3 = serious damage
4 = total destruction
ORYSA = *Oryza sativa*
CYPDI = *Cyperus difformis*
ELOAC = *Eleocharis acicularis*.

| Compound of the invention | Water application kg ai/ha | ORYSA | CYPDI | ELOAC |
|---|---|---|---|---|
| Example 1 | 0.1 | 0 | 4 | 4 |
| Example 2 | 0.1 | 0 | 4 | 4 |
| Example 3 | 0.1 | 0 | 4 | 4 |
| Example 4 | 0.1 | 0 | 4 | 4 |
| Example 6 | 0.1 | 0 | 4 | 4 |
| Example 7 | 0.1 | 0 | 4 | 4 |
| Untreated | — | 0 | 0 | 0 |

EXAMPLE B

In a greenhouse, the compounds noted in the table were applied at the rates mentioned. For this the formulated active ingredients were pipetted onto the water surface of vessels containing 1500 ml water. Test plants that were treated were in the 1 to 5 leaf stages. Three weeks after the application, the damage to the plants was assessed according to the following scheme. The compounds of the invention showed good activity against *Monochoria vaginalis*, coupled with selectivity in paddy-rice. The comparison material was weakly active.

In the following table:
0 = no damage
1 = slight damage
2 = medium damage
3 = serious damage
4 = total destruction
ORYSA = *Oryza sativa*
MOOVA = *Monochoria vaginalis*.

| Compound of the invention | Water application kg ai/ha | ORYSA | MOOVA |
|---|---|---|---|
| Example 3 | 0.05 | 0 | 4 |
| Untreated Comparison | — | 0 | 0 |
| Bensulfuron-methyl | 0.05 | 0 | 3 |

EXAMPLE C

In a greenhouse, the compounds noted in the table were applied at the rates mentioned. For this the formulated active ingredients were pipetted onto the water surface of vessels containing 1500 ml water. Test plants that were treated were in the 1 to 5 leaf stages. Three weeks after the application, the damage to the plants was assessed according to the following scheme. The compounds of the invention showed good activity against *Scirpus juncoides*, coupled with selectivity in paddy-rice. The comparison material was weakly active.

In the following table:
0 = no damage
1 = slight damage
2 = medium damage
3 = serious damage
4 = total destruction
ORYSA = *Oryza sativa*
SCPJU = *Scirpus juncoides*.

| Compound of the invention | Water application kg ai/ha | ORYSA | SCPJU |
|---|---|---|---|
| Example 3 | 0.05 | 0 | 4 |
| Untreated Comparison | — | 0 | 0 |
| Bensulfuron-methyl | 0.05 | 0 | 3 |

EXAMPLE D

In a greenhouse, the compounds noted in the table were applied at the rates mentioned. For this the formulated active ingredients were pipetted onto the water surface of vessels containing 1500 ml water. Test plants that were treated were in the 1 to 5 leaf stages. Three weeks after the application, the damage to the plants was assessed according to the following scheme. The compounds of the invention showed good activity against *Cyperus serotinus*, coupled with selectivity in paddy-rice. The comparison material was weakly active.

In the following table:
0 = no damage
1 = slight damage
2 = medium damage
3 = serious damage
4 = total destruction
ORYSA = *Oryza sativa*
CYPSE = *Cyperus serotinus*.

| Compound of the invention | Water application kg ai/ha | ORYSA | CYPSE |
|---|---|---|---|
| Example 3 | 0.05 | 0 | 4 |
| Untreated Comparison | — | 0 | 0 |
| Bensulfuron-methyl | 0.05 | 0 | 3 |

We claim:
1. 1-(Methoxypyrimidinyl)-N-nitrophenyl-1H-1,2,4-triazole-3-sulphonamide of formula I

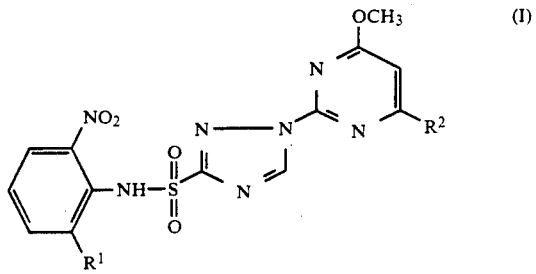

in which
$R^1$ is methyl, methoxy, allyloxy or propargyloxy, and $R^2$ is methyl or methoxy,
with the proviso that $R^1$ is not methyl, if $R^2$ is methoxy.

2. A herbicidal composition which comprises a herbicidally effective amount of a compound according to claim 1, in admixture with agriculturally acceptable carriers and diluents.

3. A method of combating weeds which comprises applying to the weeds or their locus a herbicidally effective amount of a compound according to claim 1.

4. Compound according to claim 1 in which $R^1$ is methyl or methoxy and $R^2$ is methyl.

5. Compound according to claim 1 in which $R^1$ is allyloxy or propargyloxy and $R^2$ is methyl.

6. Compound according to claim 1 in which $R^1$ is methoxy, allyloxy or propargyloxy and $R^2$ is methoxy.

7. A herbicidal composition which comprises a herbicidally effective amount of a compound according to claim 4, in admixture with agriculturally acceptable carriers and diluents.

8. A herbicidal composition which comprises a herbicidally effective amount of a compound according to claim 5, in admixture with agriculturally acceptable carriers and diluents.

9. A herbicidal composition which comprises a herbicidally effective amount of a compound according to claim 6, in admixture with agriculturally acceptable carriers and diluents.

10. A method of combating weeds which comprises applying to the weeds or their locus a herbicidally effective amount of a compound according to claim 4.

11. A method of combating weeds which comprises applying to the weeds or their locus a herbicidally effective amount of a compound according to claim 5.

12. A method of combating weeds which comprises applying to the weeds or their locus a herbicidally effective amount of a compound according to claim 6.

* * * * *